US005756864A

United States Patent [19]

Darsow et al.

[11] Patent Number: 5,756,864
[45] Date of Patent: May 26, 1998

[54] PROCESS FOR PREPARING D,L-MENTHOL FROM D-MENTHOL

[75] Inventors: Gerhard Darsow, Krefeld; Gerd-Michael Petruck, Erkrath, both of Germany

[73] Assignee: Bayer Aktiengesellschaft, Leverkusen, Germany

[21] Appl. No.: 644,883

[22] Filed: May 10, 1996

[30] Foreign Application Priority Data

May 17, 1995 [DE] Germany ............... 195 18 023.2

[51] Int. Cl.⁶ .................... C07C 27/00; C07C 35/12
[52] U.S. Cl. ........................... 568/830; 568/829
[58] Field of Search ....................... 568/829, 830; 562/324, 325

[56] References Cited

U.S. PATENT DOCUMENTS 2,843,636  7/1958  Booth .
4,058,571  11/1977  Biedermann .
5,300,706  4/1994  Immel et al. .

OTHER PUBLICATIONS

Catalysis Letters, Bd. 29, 1994, pp. 57–67, XP00201695 Allakhverdiev, et al.: "Liquid–phase stereoselective thymol hydrogenation over supported nickel catalysts".

Primary Examiner—Gary Geist
Assistant Examiner—Karl J. Puttlitz, Jr.
Attorney, Agent, or Firm—Sprung Kramer Schaefer & Briscoe

[57] ABSTRACT

A process is described for preparing D,L-menthol by catalytic rearrangement of optically active D-menthol in the presence of hydrogen at temperatures of from 200 to 350° C. and under pressures of from 50 to 350 bar over fixed-bed catalysts comprising support-free reduced shaped bodies of pressed powders of nickel, manganese, alkaline earth metal (hydr)oxides and optionally (hydr)oxides of elements of transition groups V and/or VI of the Periodic Table.

6 Claims, No Drawings

5,756,864

PROCESS FOR PREPARING D,L-MENTHOL FROM D-MENTHOL

The invention relates to a process for preparing D,L-menthol by catalytic rearrangement of optically active d-menthol in the presence of hydrogen.

L-Menthol has a special position among the naturally occurring cyclic terpene alcohols because of its cooling and refreshing action. L-Menthol is the main constituent of peppermint oil and is used in the fragrances, flavours and pharmaceuticals industries.

The preparation of menthol by catalytic hydrogenation of thymol leads to the D,L-racemate which can be resolved into its enantiomers. The 8 optically active menthols differ in respect of their organoleptic properties. L-Menthol has a characteristic peppermint odour and the refreshing action already mentioned. The racemate naturally has the advantageous properties of L-menthol only in part. As a result there was the problem of racemizing the D-menthol formed in the resolution of the racemate so as to again be able to obtain L-menthol from the newly formed racemate.

It is known from U.S. Pat. Specification No. 2 843 636 and German Auslegeschrift 2 314 813 that heating with hydrogen in the presence of a copper chromite or cobalt/manganese hydrogenation catalyst enables, inter alia, D-menthol to be racemized or the stereoisomers of menthol to be isomerized to D,L-menthol. According to EP-A 563 611, the stereoisomers of menthol can be rearranged to d,l-menthol in the presence of hydrogen over a fixed-bed catalyst containing palladium, ruthenium, rhodium or a mixture of these elements as active constituents and alkali metal hydr(hydr)oxides and/or sulphates as promoters on a support doped with a rare earth metal and manganese.

These processes of the prior art either produce too many by-products (which, particularly in a continuous procedure, cause interference owing to accumulation), or the catalysts used lose their initial activity too quickly, have limited mechanical stability, only allow limited throughput per amount of catalyst and/or make reprocessing of the used catalysts difficult.

It was therefore desirable to provide long-lived catalysts which allow high throughput per amount of catalyst for the racemization of D-menthol to D,L-menthol, which catalysts should be free of complicated support systems and therefore reprocessible.

Surprisingly, the problem indicated can be solved by means of support-free fixed-bed catalysts which can be obtained by reduction of shaped bodies of pressed metal (hydr)oxide powders. In the context of this invention, the term metal (hydr)oxide means metal (hydr)oxide and/or metal oxide.

The invention accordingly provides a continuous process for preparing D,L-menthol by catalytic rearrangement of optically active D-menthol in the presence of hydrogen under elevated pressure and at elevated temperature, characterized in that the rearrangement is carried out at a hydrogen pressure of from 50 to 350 bar, preferably from 100 to 300 bar, and temperatures of from 200° to 350° C., preferably from 220° to 290° C., in a fixed-bed process over support-free shaped bodies which act as catalysts and are obtainable by reduction of shaped bodies of pressed powders of nickel, manganese and alkaline earth metal (hydr)oxides and optionally (hydr)oxides of elements of transition groups V and/or VI of the Periodic Table.

The catalysts to be used according to the invention allow a notable throughput per amount of catalyst:

If merely support-free shaped bodies of pressed powders of nickel, manganese and alkaline earth metal (hydr)oxides are used, the possible weight hourly space velocity over the catalyst is between 400 and 1000 g of D-menthol per liter of catalyst. If pressed powders of (hydr)oxides of elements of transition groups V and/or VI of the Periodic Table are used in addition, the weight hourly space velocity over the catalyst can be increased to 1500 g of D-menthol per liter of catalyst and the reaction temperature can be reduced by up to 50° C.

The Ni contents (in each case calculated as metal) are from 30 to 60% by weight, the Mn contents are from 10 to 20% by weight, the alkaline earth metal contents are from 0.2 to 5% by weight and the contents of elements of transition groups V and/or VI of the Periodic Table are in total up to 5% by weight, preferably from 0.5 to 5% by weight. The remainder to 100% by weight is oxygen for the compounds present in oxidic form.

Suitable alkaline earth elements are especially magnesium, calcium, strontium and barium, preferably strontium and barium. Suitable elements of transition group V are preferably vanadium, niobium and tantalum, suitable elements of transition group VI are preferably chromium, molybdenum and tungsten. The elements of transition groups V and VI acting as promoters can be used either individually or as a mixture of a plurality of these elements.

The support-free shaped bodies can be produced by customary methods by pressing the metal (hydr)oxide powder mixtures (optionally after preheating at elevated temperatures), for example on tabletting or pelletizing machines, under high pressure, with graphite and/or adhesives in amounts of from 0.5 to 3% by weight, based on the total weight of the constituents to be pressed, also being able to be used to improve the adhesion of the metal (hydr)oxide particles. Examples of shaped bodies are pellets, spheres or granules having diameters of from 3 to 7 mm. Tabletted shaped bodies can also be provided with an axial hole to increase the external surface area. Viewed macroscopically, such shaped bodies have a smooth surface.

The pressed metal (hydr)oxide shaped bodies have a high compressive strength of from 300 to 800 N/cm$^2$, preferably from 400 to 600 N/cm$^2$, on the planar surface of the shaped body or from 50 to 200 N, preferably from 80 to 140 N, on the curved surface of the shaped body. The internal surface area of the pressed metal (hydr)oxide powders is from 30 to 200 m$^2$/g, preferably from 80 to 160 m$^2$/g. The compressive strength of the support-free shaped bodies can be determined in accordance with DIN 50 106, the internal surface area by the method of F. M. Nelsen and F. T. Eggertsen, Analyt. Chem. 30 (1958), 1387–1392 or S. J. Gregg and S. W. Sing, Adsorption, Surface Area and Porosity, London 1982, Chapters 2 and 6.

Before use, the shaped bodies of pressed (hydr)oxide powders have to be carefully reduced. This is preferably done using a reducing gas comprising an inert gas/hydrogen mixture in which the hydrogen content is initially from 10 to 15% by volume. Nitrogen is preferably used as inert gas. The reduction is carried out, for example, over a period of about 24 hours at a reduction temperature of from 180° to 220° C., with the proportion of nitrogen in the gas mixture being steadily reduced in the final phase of the reduction until the gas mixture finally consists entirely of hydrogen. The reduction is complete when hydrogen is no longer consumed and, as a result, water of reaction is no longer formed.

The racemization reactors can be individual high-pressure tubes of steel or a steel alloy, the tubes being completely or partially filled with the shaped bodies. In the case of relatively large tube cross-sections, the use of the support-free shaped bodies on trays (for instance wire baskets or the like) can also be useful. However, it is also possible to use high-pressure tube bundles within a common jacket, with the individual tubes again being completely or partially filled with the support-free shaped bodies.

The process of the invention using the catalysts arranged in a fixed bed can be carried out in the gas phase, a trickling phase or in a rising liquid phase. In general, molar hydrogen excesses are used, with at least a 5-fold molar amount of hydrogen per mol of starting compound passing through the reactor during the course of the process.

The process of the invention can be carried out with or without solvents. Suitable solvents which are inert under the reaction conditions are, for example, methanol, ethanol, isopropanol.

The process of the invention enables very high catalyst operating lives of from 20,000 to 25,000 hours to be achieved. These operating lives are a multiple of those described in earlier publications (e.g. German Auslegeschrift 2 314 813).

The racemization occurring in the process of the invention surprisingly proceeds so gently that the formation of unusable by-products, such as undesired hydrocarbons, is kept to <0.5% by weight.

The reaction mixture obtained has such a high content of D,L-menthol that it can be worked up to this desired product by simple distillation. In this context, it should be noted that the racemization equilibrium lies at 59.8% of L-menthol; the yields achievable according to the invention almost reach this value.

After separating off the desired D,L-menthol by distillation, the first distillation fraction together with the distillation bottoms can be returned to the reaction. The amount of starting material corresponding to the D,L-menthol taken off by distillation is replaced. The hydrogen not consumed in the process of the invention can be circulated.

After removing the first distillation fraction and the distillation bottoms, the D,L-menthol produced is obtained in a purity of ≧99.9% by weight and can therefore be used without further purification for all downstream processes.

The clear and colourless product obtained after the distillation has a melting point of 41° C. and can be crystallized in crystallization equipment of a conventional type.

In the examples below, the unit "standard $m^3$" means cubic meters converted to standard conditions (1 bar, 25° C.).

EXAMPLES

Example 1

A vertical, heat-insulated high-pressure tube of stainless, acid-resistant steel having an internal diameter of 45 mm and a length of 1 m, which had previously been flushed free of oxygen using nitrogen, was charged with 1.4 l of shaped bodies produced by tabletting powders of nickel, manganese and barium (hydr)oxides. The nickel content of the pellets was 54% by weight, the manganese content was 15% by weight, the barium content was 1.5% by weight. The pellets had a cylinder height of 5 mm, a diameter of 5 mm and a compressive strength of 450 N/cm$^2$ on the planar cylinder surface and of 120 N on the curved cylinder surface, and also an internal surface area of 158 m$^2$/g.

The pellets were first dried for 6 hours in a stream of nitrogen (temperature: max. 200° C., amount: 5 standard m$^3$ of N$_2$/h). Activation was carried out under a nitrogen pressure of 200 bar at a temperature between 180° and 220° C., with hydrogen gradually being mixed into the nitrogen, the initial proportion of hydrogen in the mixture being from 10 to 15% by volume. Over a period of 24 hours, the nitrogen content of the gas mixture was steadily reduced until finally pure hydrogen flowed through the reactor. The activation was complete as soon as no more water of reaction collected in the downstream separator.

After activation of the catalyst, the hydrogen pressure in the reactor system was increased to 300 bar. Subsequently, 1400 g/h of d-menthol (purity: 99.9% by weight) together with 10 standard m$^3$/h of hydrogen were pumped under a pressure of 300 bar from the top downwards through the high-pressure tube, with the d-menthol being heated in an upstream electrically heated heat exchanger to a temperature of 290° C. before entering the high-pressure tube.

The reaction product leaving the reaction tube was cooled in a second heat exchanger (water cooler) under 300 bar hydrogen pressure to a temperature <60° C. and separated in a gas separator from excess hydrogen which was returned to the reaction system.

The d-menthol throughput corresponded to a weight hourly space velocity over the catalyst of 1.0 kg/l of catalyst×h. After 7000 hours of operation, the catalyst was still highly active.

After removing the products having lower and higher boiling points by distillation, the d,l-menthol was obtained in a purity of 99.9% by weight.

Example 2

A high-pressure tube as in Example 1 was charged under inert gas with 1.4 l of shaped bodies produced by tabletting powders of nickel, manganese, barium and tungsten (hydr) oxides. The nickel content of the pellets was 48% by weight, the manganese content was 15% by weight, the barium content was 1.0% by weight and the tungsten content was 0.6% by weight. The pellets had a cylinder height of 5 mm, a diameter of 5 mm and a compressive strength of 545 N/cm$^2$ on the planar cylinder surface and of 110 N on the curved cylinder surface, and also an internal surface area of 117 m$^2$/g.

After the activation of this pressed metal (hydr)oxide powder mixture as in Example 1, the hydrogen pressure was increased to 300 bar.

Subsequently, 1800 g/h of D-menthol (purity: 99.9% by weight) together with 10 standard m$^3$/h of hydrogen were pumped continuously under a pressure of 300 bar from the top downwards through the high-pressure tube, with the D-menthol being heated to a temperature of 240° C. before entering the high-pressure tube.

The d-menthol throughput corresponded to a weight hourly space velocity over the catalyst of 1.29 kg/l of catalyst×h. After 6000 hours of operation, the catalyst was still highly active.

Example 3

A high-pressure tube as in Example 1 was charged under inert gas with 1.4 l of shaped bodies produced by tabletting powders of nickel, manganese, barium and molybdenum (hydr)oxides. The nickel content of the pellets was 60% by weight, the manganese content was 15% by weight, the barium content was 1.5% by weight and the molybdenum content was 1.0% by weight. The pellets had a cylinder height of 5 mm, a diameter of 5 mm and a compressive strength of 635 N/cm$^2$ on the planar cylinder surface and of 90 N on the curved cylinder surface, and also an internal surface area of 138 m$^2$/g.

After the activation of this pressed metal (hydr)oxide powder mixture as in Example 1, the hydrogen pressure was kept at 200 bar.

Subsequently, 1900 g/h of D-menthol together with 10 standard m$^3$/h of hydrogen were pumped continuously under a pressure of 200 bar from the top downwards through the high-pressure tube, with the D-menthol and the hydrogen being heated to 230° C. before entering the high-pressure tube.

The D-menthol throughput corresponded to a weight hourly space velocity over the catalyst of 1.36 kg/l of catalyst×h. After 7400 hours of operation, the catalyst was still highly active.

Example 4

A high-pressure tube as in Example 1 was charged under inert gas with 1.4 l of shaped bodies produced by tabletting powders of nickel, manganese, strontium and vanadium (hydr)oxides. The nickel content of the pellets was 54% by weight, the manganese content was 16% by weight, the strontium content was 0.9% by weight and the vanadium content was 1.2% by weight. The pellets had a cylinder height of 5 mm, a diameter of 5 mm and a compressive strength of 691 N/cm$^2$ on the planar cylinder surface and of 110 N on the curved cylinder surface, and also an internal surface area of 141 m$^2$/g.

After the activation of the catalyst as in Example 1, the hydrogen pressure was increased to 300 bar. Subsequently, 1800 g/h of D-menthol together with 15 standard m$^3$/h of hydrogen were pumped continuously under a pressure of 300 bar from the top downwards through the high-pressure tube, with the D-menthol being heated to a temperature of 260° C. before entering the high-pressure tube.

The product leaving the reaction tube was cooled to a temperature <60° C. and separated in a gas separator from excess hydrogen which was returned to the reaction system.

The throughput of the reaction mixture corresponded to a weight hourly space velocity over the catalyst of 1.3 kg/l of catalyst×h. After 2000 hours of operation, the catalyst was still highly active.

We claim:

1. Continuous process for preparing D,L-menthol by catalytic rearrangement of optically active D-menthol in the presence of hydrogen under elevated pressure and at elevated temperature, characterized in that the rearrangement is carried out at a hydrogen pressure of from 50 to 350 bar and temperatures of from 200° to 350° C. in a fixed-bed process over an unsupported shaped catalyst having a planar surface and a curved surface and having a compressive strength of from 300 to 800 N/cm$^2$ on the planar surface and from 50 to 200 N/cm$^2$ on the curved surface and an internal surface area of from 30 to 200 m$^2$/g obtainable by reduction of shaped bodies of pressed powders of nickel, manganese and alkaline earth metal (hydr)oxides and optionally (hydr)oxides of elements of transition groups V and/or VI of the Periodic Table.

2. Process according to claim 1, wherein the shaped bodies of pressed metal (hydr)oxide powders to be used for the reduction contain from 30 to 60% by weight of nickel, from 10 to 20% by weight of manganese, from 0.2 to 5% by weight of alkaline earth metal and up to 5% by weight of elements of transition groups V and/or VI of the Periodic Table (in each case calculated as metal), where the percentages are based on the total amount of metal (hydr)oxide powder mixture and the remainder to 100% by weight is oxygen.

3. Process according to claim 1, wherein the hydrogen pressure is from 100 to 300 bar.

4. Process according to claim 1, wherein the rearrangement temperature is from 220° to 290° C.

5. Process according to claim 1, characterized in that during the rearrangement of the D-menthol at least a 5-fold molar amount of hydrogen per mol of starting material passes through the reactor.

6. Process according to claim 1, characterized in that the D,L-menthol is taken by distillation from the reaction product of the rearrangement of D-menthol and the remaining reaction products are returned to the reaction.

* * * * *